US005609640A

United States Patent [19]
Johnson

[11] Patent Number: 5,609,640
[45] Date of Patent: Mar. 11, 1997

[54] PATELLA PROSTHESES

[76] Inventor: David P. Johnson, North Chew Farm, Norton Lane, Chew Magna Avon, United Kingdom, B518 8TW

[21] Appl. No.: 175,349

[22] PCT Filed: Jul. 6, 1992

[86] PCT No.: PCT/GB92/01226

§ 371 Date: Apr. 1, 1994

§ 102(e) Date: Apr. 1, 1994

[87] PCT Pub. No.: WO93/00871

PCT Pub. Date: Jan. 21, 1993

[30] Foreign Application Priority Data

Jul. 5, 1991 [GB] United Kingdom .................... 9114603

[51] Int. Cl.[6] ........................................................ A61F 2/38
[52] U.S. Cl. ........................................................ 623/20
[58] Field of Search ........................................ 628/18, 20

[56] References Cited

U.S. PATENT DOCUMENTS

| 4,158,894 | 6/1979 | Worrell | 623/20 |
| 4,355,429 | 10/1982 | Mittelmeier et al. | 3/1.911 |
| 4,944,756 | 7/1990 | Kenna | 623/20 |
| 4,964,867 | 10/1990 | Boger | 623/20 |
| 5,019,104 | 5/1991 | Whiteside et al. | 623/20 |
| 5,024,670 | 6/1991 | Smith et aL. | 623/18 |
| 5,358,529 | 10/1994 | Davidson | 623/20 |

FOREIGN PATENT DOCUMENTS

| 0013864 | 8/1980 | European Pat. Off. . | |
| 0324143 | 7/1989 | European Pat. Off. . | |
| 2615096 | 11/1988 | France . | |
| 2625096 | 6/1989 | France | 623/20 |
| 2700260 | 7/1994 | France | 623/20 |
| 3332354 | 3/1985 | Germany | 623/20 |
| 2184025 | 6/1987 | United Kingdom | 623/20 |
| 79000739 | 10/1979 | WIPO . | |
| 91/151168 | 10/1991 | WIPO . | |

OTHER PUBLICATIONS

Clayton et al., Clinical Orthopaedics and Related Research, "Patellar Complications after Total Condylar Arthroplasty", No. 170, pp. 152–155, (Oct. 1992).

Hungerford et al., Clinical Orthopaedics and Related Research, "Total Joint Arthroplasty of the Knee", No. 192, pp. 23–33, (Jan.–Feb. 1985).

Insall et al., Journal of Bone and Joint Surgery, "The Posterior Stabilized Condylar Prosthesis: A Modification of the Total Condylar Design", vol. 64–A. No. 9, pp. 1317–1323 (Dec. 1982).

Insall et al., Journal of Bone and Joint Surgery, "A Comparison of Four Models of Total Knee–Replacement Prostheses", vol. 58–A, No. 6, pp. 754–765 (Sep. 1976).

Kenna et al., "Design Rational for the Porous Coated Anatomic Total Knee System", pp. 71–88.

Lynch et al., Journal of Arthroplasty, "Extensor Mechanism Complications Following Total Knee Arthroplasty", vol. 2, No. 2, pp. 135–140 (Jun. 1987).

Merkow et al., Journal of Bone and Joint Surgery, "Patellar Dislocation Following Total Knee Replacement", vol. 67–A, No. 9, pp. 1321–1327, (Dec. 1985).

Mochizuki et al., Journal of Bone and Joint Surgery, "Patellar Complications Following Total Knee Arthroplasty", vol. 61–A, No. 6, pp. 878–883, (Sep. 1979).

Moreland et al., Clinical Orthopaedics and Related Research, "ICLH Replacement of the Knees", No. 145, pp. 47–59, (Nov.–Dec. 1979).

(List continued on next page.)

Primary Examiner—Michael J. Milano
Attorney, Agent, or Firm—Wenderoth, Lind & Ponack

[57] ABSTRACT

A patella prosthesis is a mushroom shaped member whose head (1) is symmetrical or contoured to correspond to a human patella. The stem (2) is for insertion in a drilling in the resectioned surface which is shaped to receive the inferior surface (4) of the head (1). The preferred material is polyethylene or high purity alumina ceramic and there may be a metal backing (5) with a porous surface over the inferior side (4). Hydroxyapatite coating may also be applied here.

22 Claims, 2 Drawing Sheets

OTHER PUBLICATIONS

Picetti et al., Journal of Bone and Joint Surgery, "The Patellofemoral Joint after Total Knee Arthroplasty without Patellar Resurfacing", vol. 72–A, No. 9, pp. 1378–1382, (Oct. 1990).

Ranawat, Clinical Orthopaedics and Related Research, "The Patellofemoral Joint in Total Condylar Knee Arthroplasty", No. 205, pp. 92–99, (Apr. 1986).

Ritter et al., Journal of Arthroplasty, "Effect of Range of Motion on the Success of a Total Knee Arthroplasty", vol. 2, No. 2, pp. 95–97, (Jun. 1987).

Scott et al., American Academy of Orthopaedic Surgeons, "Unicompartment Unicondylar Total Knee Replacement in Osteoarthritis of the Knee", pp. 203–204.

Scuderi et al., Journal of Bone and Joint Surgery, "Survivorship of Cemented Knee Replacements", vol. 71–B, No. 5, pp. 798–803, (Nov. 1989).

Simison et al., Journal of Bone and Joint Surgery, "Complications of the Attenborough Kness Replacemnt", vol. 68–B, No. 1, pp. 100–105, (Jan. 1986).

Sneppen et al., Acta orthop. scand. 49, "Laterial Dislocation of the Patella Following Marmor and Guepar Arthroplasty of the Knee", pp. 291–294, (1978).

Thorpe et al., Journal of Bone and Joint Surgery, "Intra–Articular Fibrous Bands", vol. 72–A, No. 6, pp. 810–814, (Jul. 1990).

Wright et al., Journal of Bone and Joint Surgery, "Total Knee Arthroplasty with the Kinematic Prosthesis", vol. 72–A, No. 7, pp. 1002–1009, (Aug. 1990).

Goodfellow et al., Clinical Orthopaedics and Related Research, "Clinical Results of the Oxford Knee", pp. 21–42.

PATELLA PROSTHESES

BACKGROUND OF THE INVENTION

1. Field of the Invention

This invention relates to surgical devices and is concerned with a prosthetic patella replacement for use as a surgical implant.

2. Description of Related Art

The surgical management of arthritis of the knee involves external supports such as bandages, braces and walking aids. Operative intervention may include anaesthetic, intra-articular steroid injection or radio-isotope synovectomy, arthroscopic washout, debridement, menisectomy, chondroplasty or synovectomy, esteotomy or an arthroplasty.

Joint arthroplasty may be an excision arthroplasty or interpositional or fascial arthroplasty or a prosthetic arthroplasty. Prosthetic arthroplasty of the knee may be undertaken as a uni-compartmental arthroplasty, a bi-compartmental arthroplasty, a patello-femoral arthroplasty or a total knee arthroplasty. The total knee arthroplasty may be subdivided into a hinged or linked arthroplasty although this has been superseded by the total condylar arthroplasty which may be unconstrained, semi-constrained or constrained according to the freedom of motion conferred upon the arthroplasty by its design (Goodfellow and O'Connor 1986).

Patello-Femoral replacement was not initially performed as a part of total knee arthroplasty (Sneppen et al 1978). The anterior surface of the femur was left uncovered articulating directly with the patella. This resulted in unacceptable knee pain and poor function. Therefore modifications were introduced which resurfaced the anterior surface of the femur (Insall et al 1976). This still resulted in unacceptable anterior knee pain and poor function. Therefore a patella prosthesis was developed which was initially a polyethylene dome shape fitting flush on top of the patella after the articular surface was resected (Moreland Thomas and Freeman 1979). A small keel or peg was fitted down in the cancellous bone of the patella to stabilise the prosthesis onto the bone. This patella dome was cemented in situ with acrylic cement (Install, Lachiewich and Burstein 1982, Wright et al 1990).

As un-cemented prostheses became popular in the early 1980's the design of the patella was changed in most implants (Hungerford and Krackow 1985). The basic concept was unaltered. However, a metal back was attached to the implant to reduce deformation of the polyethylene, to allow initial fixation without acrylic cement and to allow bone ingrowth into the porous metal backing of the patella thus giving long term stability within the bone (Kenna and Hungerford 1984). However the recent reports now emerging throughout the world refer to great problems with such a design. As the polyethylene thickness is reduced to allow for the metal backing, the polyethylene becomes liable to disintegrate under the stresses to which it is submitted. The wear rate progresses through the thin polyethylene at an earlier stage, the metal backing may then be exposed and cause squeaking or scratching of the implant and metallic debris may be added to the plentiful polyethylene debris produced. The manufacture of the metal backing has been difficult, leading to disruption of the pegs from its reverse side. The metal backing and the polyethylene may become dissociated, and manufacture of a harder carbon fibre impregnated polyethylene patella dome has led to excessive wear, release of carbon fibre into the knee and disruption of the polyethylene due to faulty manufacture. Patella fracture of dislocation may also occur and this may be more common with the thicker designs of patella implant or where insufficient patella bone is resected (Scott et al 1978, Mochizuki and Schurman 1979, Clayton and Thirupathi 1982, Ranawat 1986, Simison, Noble and Hardinge 1986, Lynch, Rorabeck and Bourne 1987).

The incidence of patello-femoral complications following knee arthroplasty is now the most common complication and has been reported as being up to 64% of cases (Sneppen et al 1978, Clayton and Thirupathi 1982, Merkow, Soudry and Insall 1985, Scuderi et al 1989).

Another factor which has received little attention is the shape of the articulating surface in relation to patello-femoral stability in the lateral plane. It is accepted that the anterior flange of the femoral component must be long enough to prevent lateral tracking or soft tissue impingement (Sneppen et al 1978, Thorpe, Bocell and Tullos 1990). Hungerford suggested an anatomical shape of patella button with the maximal thickness placed laterally. However the use of this implant fell into disrepute with the difficulties of insertion and high complication rate (Kenna and Hungerford 1984, Hungerford and Krackow 1985). Recently a design has been released with a central post and a surrounding shelf at a lower level. This was produced to aid patello-femoral stability by increasing the lateral resistance to patella subluxation from the patello-femoral groove. The incidence of patello-femoral complications has led many surgeons to abandon patella resurfacing (Scott et al 1978, Picetti, McGann and Welch 1990).

There has been little concern with the mechanics of the human patella in relationship to the articular geometry. Thus the patella is a torque converter between the pull vertically of the quadriceps muscle and the patella tendon acting on the tibial to extend the knee joint. The patella articulates at its thickest inferior pole in knee extension thus maintaining the point of articulation within the depth of the patella groove distally where it is more stable, but also shifting the quadriceps tendon anteriorly thus increasing the moment around the knee and generating a greater extension force on the tibia near full extension. This produces an advantageous mechanical advantage to the quadriceps and also confers greater stability to the patello-femoral joint.

The human patella during knee flexion articulates upon its medical and lateral edges, so allowing the patella to sink between the femoral condyles and a greater range of knee flexion for a given quadriceps flexibility. The articulation on the patella shifts to the superior portion which is thinner and allows sinkage between the condyles. But it also allows less patella flexion during knee flexion and hence further knee flexion for a given quadriceps flexibility (Ritter and Campbell 1987).

SUMMARY OF THE INVENTION

The aim of the invention is to design an implant using materials which will be subject to less wear, less subject to disintegration under stress, and less likely to become disrupted from any metal backing. It should also allow a greater thickness of the implant to prolong its longevity, but without increasing the thickness of the whole patella-implant complex and without weakening the construction. It should further be possible to allow un-cemented insertion of the implant, and further objects are to enable reconstruction of the anatomical patella to have a shape which allows sinkage between the condyles during knee flexion, to minimise the patella flexion during knee flexion, to increase the extensor moment during knee extension, and to increase patello-femoral stability.

According to one aspect of the present invention there is provided a patella prosthesis comprising a generally mushroom shaped member whose stem is received in a countersunk hole in the surface of a re-sectioned patella articular surface.

The preferred materials are polyethylene and high purity alumina ceramic.

A metal backing with a porous surface may be provided on the inferior side of the prosthesis. Also, a hydroxyapatite coating may be applied to this side, either to the main material or to the metal backing if that is provided.

In a simple form, the prosthesis is symmetrical about the axis of the mushroom-shaped member. However, it will generally be preferred to have the head of this member asymmetrical and shaped to follow closely the contours of the human patella.

According to another aspect of the present invention there is provided a method of manufacturing a patella prosthesis comprising scanning a patient's patella to make a record of the contours and then constructing a patella prosthesis using said record to reproduce the contours on a workpiece.

Such a patella prosthesis will of course be as defined above.

According to a further aspect of the present invention there is provided a method of implanting a patella prosthesis comprising carrying out a patella articular resection, drilling the surface thus formed, and implanting a patella prosthesis as defined above with the stem inserted in the drilling.

For a better understanding of the invention some embodiments will now be described, by way of example, with reference to the accompanying drawings, in which:

DETAILED DESCRIPTION OF THE FIGURES

Figure 1:
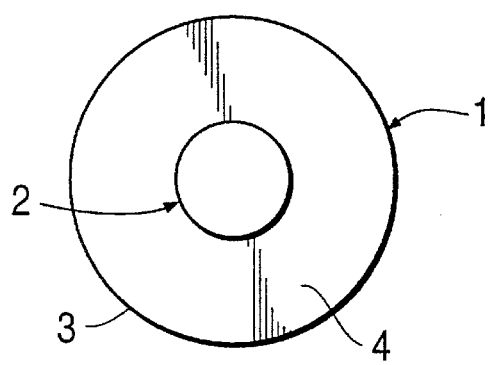
FIG. 1 is an inferior view of a patella dome.

All the domes are generally of squat mushroom shape with a head 1 and a stem 2. They differ primarily in the contours of the head and in the materials in which they are made. Typically, the diameter of the head might be 20–30 mm, the depth of the head from crown to the end of the slope 6–10 mm, the depth of the shallow cylindrical portion of the head (or edges 3) 3 mm, the diameter of the stem 10 mm and its length 4 mm.

Figure 2:
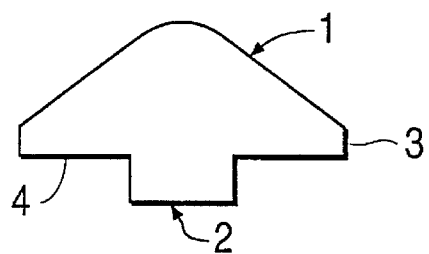
FIG. 2 is a lateral view of a patella dome.

In FIGS. 1 and 2, the dome of the patella prosthesis is of conventional symmetrical shape.

It can be manufactured from polyethylene or from high purity alumina ceramic. The latter is particularly resistant to wear and so the production of wear debris and disruption is minimised.

After patella articular surface resection the surface is further drilled to allow the stem 2 to be countersunk, thus providing an implant with a thicker articular surface whilst not increasing the overall thicknes of the construct. These two versions are fixed with acrylic cement.

Figure 3A:
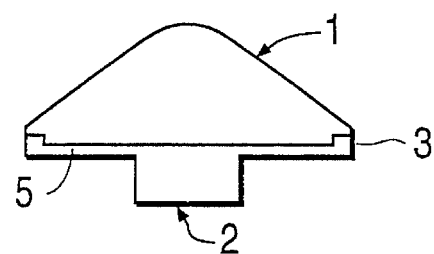
FIGS. 3a and 3b are lateral views of a patella dome such as that of FIG. 1.
Figure 3B:
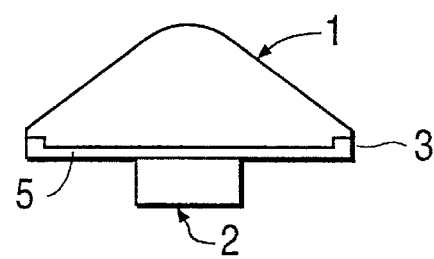

A third version has a hydroxyapatite coating to the narrow cylindrical edge 3 and inferior side 4 of the head 1 and to the stem 2, thus allowing for tissue integration and uncemented use. A fourth version, shown in FIG. 3a, is generally similar in overall dimensions but has an incorporated metal backing 5 with a porous metal surface (which may not extend over the stem 2 as seen in FIG. 3b) and hydroxyapatite coating, for uncemented use.

Figure 4:
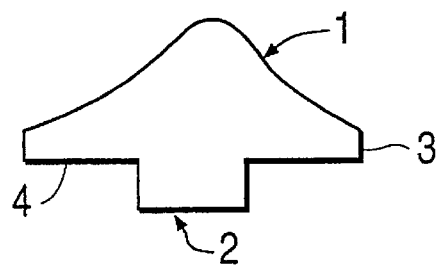
FIG. 4 is a coronal view of a patella dome for improved torque conversion.
Figure 5:
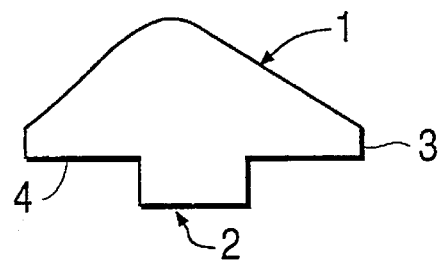
FIG. 5 is a sagittal view of the dome of FIG. 4.
Figure 6:
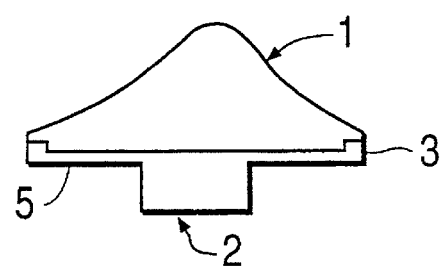
FIG. 6 is a coronal view of another torque converter patella dome.
Figure 7:
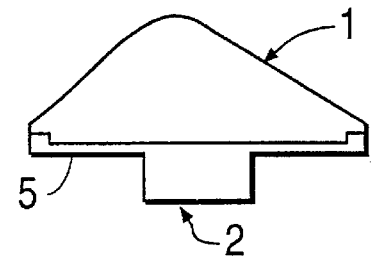
FIG. 7 is a sagittal view of the dome of FIG. 6.

A second type of patella implant, shown in FIGS. 4 and 5 and in FIGS. 6 and 7, is modified from the first type described above by having an eccentric dome more akin to the shape of the human patella. This I refer to as the 'Torque Converter Patella Dome' (TPD). Again it can be manufactured from polyethylene or high purity alumina ceramic, with or without a hydroxyapaptite coating to the sides and base, or (as in FIGS. 6 and 7) with a ceramic articulating surface having a metal backing with a porous surface and a hydroxyapatite coating.

A third type of patella implant is for patients who have isolated patello-femoral arthritis at an early age and in whom total condylar knee arthroplasty can be avoided by patella resurfacing in isolation. The three dimensional anatomy of a patient's patella is taken from a scan of the patella, either from the pictures of a computerised tomography scan or alternatively a magnetic resonance imaging scan of the in situ arthritic patella. What I refer to as an 'Elite Custom Patella Dome' (EDPD) is then constructed by computer assisted manufacturing techniques for implantation in the patient. Each implant is therefore a customised model of the patient's original patella. In materials and appearance there will not be any great difference between this type and the second type of FIGS. 4 to 7 and therefore they are not illustrated.

I claim:

1. A patella prosthesis comprising:
   a body portion having an articulating side, a patella connection side, a first surface on said articulating side and a second surface on said patella connection side, wherein said first surface has a single rounded projection which is asymmetrical with respect to both coronal and sagittal views, and
   an anchor stem projecting from said second surface in a direction away from said first surface for reception in a hole countersunk in a surface of a patella articular surface.

2. The patella prosthesis according to claim 1, wherein said body portion comprises alumina.

3. The patella prosthesis according to claim 1, wherein said second surface is provided with a hydroxyapatite coating.

4. The patella prosthesis according to claim 1, which further comprises a metal backing having a porous surface which is fixed to said second surface of said patella connection side.

5. The patella prosthesis according to claim 4, wherein said first surface and said second surface have first and second outer perimeters, respectively, which are spaced apart to define a shoulder of said body portion.

6. The patella prosthesis according to claim 5, wherein said metal backing has an outer perimeter and a circumferential lip projecting from said outer perimeter towards said first surface along said shoulder, and wherein an external diameter of said circumferential lip does not exceed an external diameter of said body portion.

7. The patella prosthesis according to claim 5, wherein said shoulder is about 3 mm in depth.

8. The patella prosthesis according to claim 1, wherein said anchor stem on said patella connection side is implanted into a resectioned surface of a patient's patella.

9. The patella prosthesis according to claim 1, wherein said first surface of said articulating side is shaped to follow closely the contours of a patient's scanned patella.

10. The patella prosthesis according to claim 1, which is designed according to the steps of (a) determining a profile of the prosthesis by scanning a patient's patella and making a record of the contours of said patella from the scan, and (b) constructing a patella prosthesis using said profile record to reproduce the contours on a workpiece.

11. The patella prosthesis according to claim 4, which further comprises a metal backing having a porous surface which is fixed to said second surface of said patella connection side and fixed to said anchor stem.

12. A patella prosthesis comprising:

a body portion having an articulating side, a patella connection side, a first surface on said articulating side and a second surface on said patella connection side, said first surface and said second surface having first and second outer perimeters, respectively, which are spaced apart to define a shoulder of said body portion, an anchor stem projecting from said second surface in a direction away from said first surface for reception in a hole countersunk in a surface of a patella articular surface, and a metal backing having a porous surface which is fixed to said second surface of said patella connection side, wherein said metal backing has an outer perimeter and a circumferential lip projecting from said outer perimeter towards said first surface along said shoulder, and wherein an external diameter of said circumferential lip does not exceed an external diameter of said body portion.

13. The patella prosthesis according to claim 12, wherein said shoulder is about 3 mm is depth.

14. The patella prosthesis according to claim 12, wherein said body portion comprises alumina.

15. The patella prosthesis according to claim 12, wherein said first surface has a single rounded projection which is asymmetrical with respect to both coronal and sagittal views.

16. The patella prosthesis according to claim 12, wherein said anchor stem on said patella connection side is implanted into a resectioned surface of a patient's patella.

17. The patella prosthesis according to claim 12, wherein said first surface of said articulating side is shaped to follow closely the contours of a patient's scanned patella.

18. The patella prosthesis according to claim 12, which is designed according to the steps of (a) determining a profile of the prosthesis by scanning a patient's patella and making a record of the contours of said patella from the scan, and (b) constructing a patella prosthesis using said profile record to reproduce the contours on a workpiece.

19. The patella prosthesis according to claim 12, which further comprises a metal backing having a porous surface which is fixed to said second surface of said patella connection side and fixed to said anchor stem.

20. A patella prosthesis for insertion in a patient's patella, said prosthesis comprising:

a body portion having an articulating side, a patella connection side, a first surface on said articulating side and a second surface on said patella connection side, wherein said first surface has a single rounded projection which is asymmetrical with respect to both coronal and sagittal views, and a single anchor stem projecting from said second surface in a direction away from said first surface for reception in a hole countersunk in a surface of a patella articular surface.

21. The patella prosthesis according to claim 20, wherein the contour of said first surface of said articulating side is determined by the patient's patello-femoral anatomy.

22. A patella prosthesis for insertion in a patient's patella, said prosthesis comprising:

a body portion having an articulating side, a patella connection side, a first surface on said articulating side and a second surface on said patella connection side, wherein said first surface has a single rounded projection which is asymmetrical with respect to both coronal and sagittal views, and a single anchor stem projecting from said second surface in a direction away from said first surface for reception in a hole countersunk in a surface of a patella articular surface, wherein the contour of said first surface of said articulating side is determined by the patient's patello-femoral anatomy, and wherein said body portion comprises alumina.

* * * * *